United States Patent [19]

Stowe

[11] 4,387,056

[45] Jun. 7, 1983

[54] PROCESS FOR SEPARATING ZERO-VALENT NICKEL SPECIES FROM DIVALENT NICKEL SPECIES

[75] Inventor: Gerald T. Stowe, Orange, Tex.

[73] Assignee: E. I. Du Pont de Nemours and Company, Wilmington, Del.

[21] Appl. No.: 254,780

[22] Filed: Apr. 16, 1981

[51] Int. Cl.³ .............................................. C07F 15/04
[52] U.S. Cl. .................................. 260/439 R; 252/414
[58] Field of Search ...................... 260/439 R; 252/414

[56] References Cited

U.S. PATENT DOCUMENTS

| | | | |
|---|---|---|---|
| 3,536,748 | 10/1970 | Drinkard, Jr. et al. | 260/439 R X |
| 3,538,142 | 11/1970 | Drinkard, Jr. et al. | 260/439 R X |
| 3,547,964 | 12/1970 | Olivier | 260/439 R X |
| 3,641,076 | 2/1972 | Booth | 260/439 R X |
| 3,669,999 | 6/1972 | Levine | 260/439 R |
| 3,676,481 | 7/1972 | Chia | 260/439 R X |
| 3,766,231 | 10/1973 | Gosser et al. | 260/439 R |
| 3,766,237 | 10/1973 | Chia et al. | 260/439 R X |
| 3,773,809 | 11/1973 | Walter | 260/465.8 R |
| 3,800,000 | 3/1974 | Fahey | 260/439 R X |
| 3,847,959 | 11/1974 | Shook, Jr. et al. | 260/439 R |
| 3,903,120 | 9/1975 | Shook, Jr. et al. | 260/439 R |

*Primary Examiner*—Helen M. S. Sneed

[57] ABSTRACT

Separating active nickel hydrocyanation catalyst from deactivated catalyst by contact with selected solvents.

7 Claims, No Drawings

PROCESS FOR SEPARATING ZERO-VALENT NICKEL SPECIES FROM DIVALENT NICKEL SPECIES

BACKGROUND OF THE INVENTION

1. Field of the Invention

The present invention relates to the recovery of active catalyst from the process streams obtained from the hydrocyanation of olefins and the isomerization of certain nitriles and, more particularly, is directed to a process for separating zero-valent nickel catalyst from deactivated nickel catalyst prior to recycle of the active catalyst to the process.

2. Description of the Prior Art

Several patents disclose processes to which the present invention may be applied. One such process is an isomerization as disclosed in U.S. Pat. Nos. 3,853,948, issued on Dec. 10, 1974, and 3,536,748, issued on Oct. 27, 1970. Another process is disclosed in U.S. Pat. No. 3,496,215, issued on Feb. 17, 1970, and involves a process for the addition of one molecule of hydrogen cyanide to an olefin such as butadiene to produce a nonconjugated, ethylenically unsaturated organic nitrile, e.g., 3-pentenenitrile, 4-pentenenitrile (collectively referred to as 3,4-PN's), and 2-methyl-3-butenenitrile (2-M-3-BN). These patents do not disclose the use of promoters with the zero-valent nickel catalyst.

A method for the separation of organic phosphorus compounds and their metal complexes from organic nitriles in the hydrocyanation of olefins is disclosed in U.S. Pat. No. 3,773,809, issued on Nov. 20, 1973. The patentee discloses a process for separating organic phosphorus compounds and certain metal complexes from the hydrocyanation product fluid containing predominantly organic dinitriles and unreacted organic mononitriles by contacting the product with a cycloparaffin or paraffin hydrocarbon. The patentee teaches that his process is dependent upon the formation of a multi-liquid phase mixture upon contact with the hydrocarbon solvent. This multiphase mixture is assured by maintaining the molar ratio of organic mononitrile to organic dinitrile less than about 0.65 and preferably less than about 0.3. The patentee notes that in the multiphase mixture formed, organic phosphorus compounds and their zero-valent nickel complexes are found predominantly in the hydrocarbon solvent phase whereas organic mono- and dinitriles, catalyst promoter, catalyst promoter residue and degraded nickel catalyst are found predominantly in at least one other phase distinct from the hydrocarbon phase, (see Col. 3, lines 15–22 of the patent). The patentee further discloses that some of the degradation products of the hydrocyanation reaction as well as degraded nickel catalyst which may be at least partially in the form of nickel cyanide and nickel halide are soluble in the organic mononitriles and dinitriles while others are precipitated therefrom. In Example 6 the patentee discloses that the organic phosphorus compounds and nickel are predominantly found in the light (hydrocarbon) phase whereas the dinitriles, e.g., adiponitrile as well as the mononitriles, e.g., pentenenitriles, are found predominantly in the heavy dinitrile phase while degraded nickel catalyst tends to collect in the dinitrile phase as an insoluble residue. The patentees do not disclose at what point the catalyst solids are formed, if indeed, they are formed by the process disclosed. The patentee requires the formation of at least two liquid phases in the practice of his process.

SUMMARY OF THE INVENTION

A process for separating zero-valent nickel species from divalent nickel species, each of which species are contained in a solution of a predominantly organic phosphorus compound which solution also contains minor amounts of mononitriles and less than 10% by weight of dinitriles based on the weight of solution, which process comprises contacting the solution with a solvent in an amount sufficient to form a precipitate while maintaining a single liquid phase and thereafter separating the precipitate from the liquid.

DETAILED DESCRIPTION OF THE INVENTION

The process of the present invention can be applied to a variety of nitrile-containing streams but is principally applied to the product fluids obtained from the addition of one molecule of hydrogen cyanide to a molecule of an olefin, e.g., butadiene and particularly to the process described in U.S. Pat. No. 3,496,215 discussed hereinabove. Another reaction product or product fluid to which the present invention is particularly applicable is that obtained by the catalytic isomerization of 2-methyl-3-butenenitrile to a linear pentenenitrile as disclosed in U.S. Pat. Nos. 3,853,948 and 3,856,748 all discussed hereinabove. A particular characteristic of all the above processes except those disclosed in U.S. Pat. No. 3,773,809 is that the commonly known promoters, e.g., zinc and organo boron compounds of the formula $BR_3$ are not employed with the zero-valent nickel catalyst. Although it is preferred to apply the process of the present invention to the above described products or to concentrates and/or mixtures of the above, the present process is applicable to any stream obtained from the hydrocyanation and/or isomerization wherein the amount of dinitrile is maintained at less than 10% by weight based upon the total weight of the product fluid. A typical stream from the above described process has the composition given in Table I after a major portion of the volatile products and/or reactants in the product stream have been removed.

TABLE I

| Component | Amount (weight %) |
| --- | --- |
| Ligand (organic phosphorous compound) | 70–85 |
| Nickel (as $Ni^0$) | 0.5–1.5 |
| Mononitriles (principally 3,4-PN's) | 5–21 |
| Dinitriles (e.g., adiponitrile) | <10 |
| Nickel (as Ni(II)) | 0.3–1 |

More particularly, the types of catalysts used in the above described process to which the process of the present invention is applied are described in U.S. Pat. No. 3,903,120, issued on Sept. 2, 1975. The preferred types of zero-valent nickel catalyst are those having the general formula $NiL_4$ where L is a neutral organophosphorus ligand such as a triarylphosphite of the formula $P(OAr)_3$ where Ar is an aryl group of up to 18 carbon atoms. Illustrative of the aryl groups are methoxyphenyl, tolyl, xylyl and phenyl. Meta- and para-tolyl and mixtures thereof are the preferred aryl groups. In the above described hydrocyanation and isomerization reactions, it is preferred to employ an excess and in many instances a substantial excess of the above-described organophosphorus ligands. The present invention is particularly applicable to those streams which contain excess ligand.

During isomerization and/or hydrocyanation a portion of the zero-valent nickel catalyst is degraded to an inactive species which is a form of nickel cyanide. This inactive nickel hinders the performance of the active catalyst and can under certain conditions form solids in the otherwise liquid system. The presence of these inactive nickel species has been recognized for example in U.S. Pat. No. 3,773,809. It is therefore desirable to separate the inactive nickel species from the catalytically active zero-valent nickel to permit direct recycle of the active nickel to the aforementioned reactions without extensive purification and without the need for phase separation.

Solvents which are operable in the present process include alkanes having 5-9 carbon atoms, e.g., pentane, hexane, heptane, octane, and nonane; cycloalkanes having 5-8 carbon atoms, e.g., cyclopentane, cyclohexane, methylcyclohexane and cyclooctane; halohydrocarbons having 1-3 carbon atoms, e.g., chloroform, dichloroethane, carbontetrachloride, dichloromethane and chloropropane; nitriles having 2-5 carbon atoms, e.g., acetonitrile, propionitrile, valeronitrile, pentenenitriles; aromatic and substituted aromatics having 6-9 carbon atoms, e.g., benzene, toluene, xylene, ethylbenzene, and isopropylbenzene. In general, the solvents are selected from the class consisting of hydrocarbons having 5-9 carbon atoms, halohydrocarbons having 1-3 carbon atoms, nitriles having 2-5 carbon atoms and mixtures of the foregoing which are nonoxidizing, nonbasic and nonhydroxylic. The preferred solvents are aliphatic and cycloaliphatic hydrocarbons.

The amount of solvent employed in the present process is not critical provided that sufficient solvent is used to precipitate the Ni(II) species. In most circumstances, and particularly when treating streams which are described hereinabove, it has been found that from 0.1-5 and preferably from 0.2-2 parts by weight of solvent per part of the stream to be treated, are satisfactory.

The temperature at which the solvent and process stream are contacted is not critical to the present invention. Temperatures generally can vary from 0°-100° C., usually from 10°-70° C. and preferably at about 25°-50° C.

Extensive mixing of the solvent and process stream is not necessary although sufficient agitation should be provided to permit thorough contact of the solvent and process stream. The resulting precipitate can be separated from the soluble material by methods known to those skilled in the art, e.g., by filtration or centrifugation.

The following examples are presented to illustrate but not to restrict the present invention. Parts and percentages are by weight unless otherwise noted. Although reference is made in the foregoing examples to the use of a specific catalyst, i.e., tetrakis(tritolylphosphite) nickel catalyst dissolved in excess tritolylphosphite (TTP) in a process involving the addition of one molecule of hydrogen cyanide to butadiene to produce 3- and 4-pentenenitriles (3,4-PN's or PN's) and the isomerization of 2-methyl-3-butenenitrile (2-M-3-BN), it is understood that the present process is applicable to the broad range of catalysts and processes as specified hereinabove.

EXAMPLES 1-7

A hydrocyanation of butadiene is conducted according to the teachings of U.S. Pat. No. 3,496,215 by continuously introducing butadiene, hydrogen cyanide and catalyst into an agitated reactor at a temperature of from 110°-145° C. and autogeneous pressure. The butadiene and hydrogen cyanide are introduced as liquids into the reactor. The liquid catalyst is prepared by reacting a mixture containing 77% TTP, 20% PN's, 3% nickel powder, to which mixture is added 100 ppm chloride catalyst as phosphorous trichloride. The mixture is heated for sixteen hours at 80° C., cooled and filtered to yield a solution containing approximately 2.7% by weight zero-valent nickel (Ni°). The catalyst preparation reaction product is mixed with TTP, which is prepared by reacting phosphorous trichloride with commercial meta-, para-cresol which contains minor amounts of related phenols, so that the catalyst feed TTP/Ni° mol ratio is approximately 10/1. The HCN/butadiene feed mol ratio is maintained at about 0.80 and the HCN/Ni° feed mol ratio is maintained at about 25/1 but both may vary. The product from the hydrocyanation reactor is continuously removed and subjected to reduced pressure to remove unreacted butadiene and volatile reaction products, (mostly 3,4-PN's and 2-M-3-BN). The amount removed depends on the HCN/butadiene mol ratio. The non-volatile portion of the product containing mostly catalyst and excess TTP is returned to the reactor. During the reaction, less than 5% of the active Ni° is deactivated. In order to replenish this catalyst and to remove deactivated catalyst on a continuous basis, a small amount of the non-volatile product fluid is purged from the return stream and replaced with the approximate equivalent of fresh catalyst prepared as described above. The purge is retained and combined with a purge produced as described below.

The volatile portion of the product from the hydrocyanation as above described, i.e., 3,4-PN's and 2-M-3-BN is treated to separate the 2-M-3-BN from the 3,4-PN's. The 2-M-3-BN is then introduced into a stirred reactor along with the catalyst prepared as described above so that the 2-M-3-BN/Ni° mol ratio is about 100/1, but may vary. The product fluid is continuously removed from the isomerization reactor and subjected to reduced pressure to recover the more volatile portion of the product (principally 3,4-PN's), the non-volatile portion containing mostly catalyst is returned to the reactor. As in the above described hydrocyanation, a portion of the active nickel Ni° is deactivated and in order to replenish the active catalyst, make-up catalyst is introduced into the returning stream as above described and a purge removed to control the level of deactivated catalyst. This purge is combined with the purge obtained from the above described hydrocyanation. Typical analyses of the combined purge stream are shown in Examples 1, 2 and 7 of the accompanying Table II.

The indicated amount of purge catalyst is then contacted by shaking with the type and amount of solvent indicated in Table II at 25° C., whereupon a precipitate is formed. The liquid and solids are separated by centrifugation and the centrate and/or solids analyzed for total nickel and zero-valent nickel present to determine the amount of spent nickel removed. The results are reported in Table II.

TABLE II

| Example No. | Purge Amount (gms) | Purge Component (% by weight) TTP | Purge Component Mono-Nitriles | Purge Component Di-Nitriles | Purge Component Total Ni | Purge Component Ni⁰ | Spent Catalyst as Ni[1] | Solvent Type | Solvent Amount (gms) | Ni in Solids (gms) | Centrate Amount (gms) | Centrate Component (% by weight) Total Ni | Centrate Component Ni⁰ | Ni⁰ recovered (%) | Spent Catalyst removed (%) |
|---|---|---|---|---|---|---|---|---|---|---|---|---|---|---|---|
| 1 | 55.4 | 82.3 | 9.0 | 3.6 | 1.27 | 0.655 | 0.615 | Cyclohexane | 18.9 | n.a.[2] | 71.3 | 0.62 | 0.55 | 108[3] | 85 |
| 2 | 53.1 | 73.5 | 20.7 | 3.1 | 1.24 | 0.624 | 0.616 | Heptane | 33.8 | n.a. | 84.2 | 0.48 | 0.38 | 97 | 74 |
| 3 | 32.76 | n.a. | n.a. | n.a. | 1.14 | 0.55 | 0.59 | Cyclohexane | 27.62 | 0.160 | 57.10 | n.a. | 0.30 | 95 | 83 |
| 4 | 33.3 | n.a. | n.a. | n.a. | 1.14 | 0.55 | 0.59 | Toluene | 29.81 | 0.165 | 60.38 | n.a. | 0.27 | 89 | 84 |
| 5 | 32.4 | n.a. | n.a. | n.a. | 1.14 | 0.55 | 0.59 | Pentenenitrile | 30.20 | 0.143 | 60.87 | n.a. | 0.28 | 96 | 75 |
| 6 | 32.47 | n.a. | n.a. | n.a. | 1.14 | 0.55 | 0.59 | Dichloromethane | 48.93 | 0.148 | 79.21 | n.a. | 0.22 | 98 | 77 |
| 7 | 55.1 | 82.3 | 9.0 | 3.6 | 1.27 | 0.655 | 0.615 | Cyclohexane | 11.4 | n.a. | 64.5 | 0.70 | 0.56 | 100 | 73 |

[1]Total Ni − Ni⁰
[2]n.a. = not analyzed
[3]Analytical variance

I claim:

1. A process for separating zero-valent nickel species from divalent nickel species each in a solution of predominantly an organic phosphorus compound along with minor amounts of mononitriles and less than 10% by weight of dinitriles based upon the weight of said solution which comprises contacting said solution with a solvent selected from the class consisting of hydrocarbons having 5-9 carbon atoms, halohydrocarbons having 1-3 carbon atoms, nitriles having 2-5 carbon atoms and mixtures of the foregoing in an amount sufficient to form a precipitate and a single liquid phase and thereafter separating the precipitate from the liquid.

2. A method for recovery of active catalyst in a process for the production of pentenenitriles wherein a zero-valent nickel complexed with an organic phosphorus compound is used as a catalyst and wherein the reaction products are treated to remove a major portion of the pentenenitriles produced resulting in a liquid composition comprising predominantly zero-valent nickel, divalent nickel species and organic phosphorus compound along with minor amounts of pentenenitriles and dinitriles, the improvement which comprises maintaining the amount of dinitrile in said liquid composition less than about 10% by weight based upon the weight of said composition and contacting said composition with a solvent selected from the class consisting of hydrocarbons having 5-9 carbon atoms, halohydrocarbons having 1-3 carbon atoms, nitriles having 2-5 carbon atoms and mixtures of the foregoing in an amount sufficient to cause at least a portion of the divalent nickel species to precipitate while maintaining a single liquid phase and thereafter separating said solid from said liquid.

3. The process of claims 1 or 2 wherein the solvent is selected from the class of aliphatic and cycloaliphatic hydrocarbons having 5-9 carbon atoms and mixtures thereof.

4. The process of claim 1 wherein 0.1-5 parts by weight of solvent are contacted with one part by weight of said solution.

5. The process of claim 2 wherein 0.1-5 parts by weight of solvent are contacted with one part by weight of said solution.

6. The process of claims 4 or 5 wherein the solvent is selected from the class consisting of aliphatic and aromatic hydrocarbons having 5-9 carbon atoms and mixtures thereof.

7. The process of claim 5 wherein the solvent is cyclohexane.

* * * * *